(12) United States Patent
Chin et al.

(10) Patent No.: US 10,335,279 B2
(45) Date of Patent: Jul. 2, 2019

(54) METHOD AND DEVICE FOR TREATING DYSFUNCTIONAL CARDIAC TISSUE

(71) Applicant: BioVentrix, Inc., San Ramon, CA (US)

(72) Inventors: Sing-Fatt Chin, Union City, CA (US); Lon Annest, New York, NY (US); Robert O'Reilly, Lafayette, CA (US)

(73) Assignee: BioVentrix, Inc., San Ramon, CA (US)

( * ) Notice: Subject to any disclaimer, the term of this patent is extended or adjusted under 35 U.S.C. 154(b) by 466 days.

(21) Appl. No.: 15/043,274

(22) Filed: Feb. 12, 2016

(65) Prior Publication Data

US 2016/0262891 A1   Sep. 15, 2016

Related U.S. Application Data

(60) Continuation of application No. 13/966,049, filed on Aug. 13, 2013, now Pat. No. 9,259,319, which is a
(Continued)

(51) Int. Cl.
*A61F 2/24* (2006.01)
*A61B 17/122* (2006.01)
(Continued)

(52) U.S. Cl.
CPC ...... *A61F 2/2487* (2013.01); *A61B 17/00234* (2013.01); *A61B 17/0469* (2013.01);
(Continued)

(58) Field of Classification Search
CPC .... A61F 2/2478; A61F 2/2481; A61F 2/2487; A61B 17/12; A61B 17/12009;
(Continued)

(56) References Cited

U.S. PATENT DOCUMENTS

| 4,007,743 A | 2/1977 | Blake |
| 5,295,958 A | 3/1994 | Shturman |

(Continued)

FOREIGN PATENT DOCUMENTS

| EP | 1 078 644 A1 | 2/2001 |
| WO | 00/06028 A1 | 2/2000 |

(Continued)

OTHER PUBLICATIONS

European Examination Report of EP Patent Application 12837466.7 dated Jun. 6, 2016, 14 pages.
(Continued)

*Primary Examiner* — Carrie R Dorna
(74) *Attorney, Agent, or Firm* — Kilpatrick Townsend & Stockton LLP

(57) ABSTRACT

Various methods and devices are provided for reducing the volume of the ventricles of the heart. In one embodiment, a method for reducing the ventricular volume of a heart chamber is provided including the steps of inserting an anchoring mechanism onto dysfunctional cardiac tissue, deploying one or more anchors into the dysfunctional cardiac tissue, raising the dysfunctional cardiac tissue using the anchors, and securing the anchors to hold the dysfunctional cardiac tissue in place. Further, a device for reducing the volume of the ventricles of a heart chamber is provided where the device has one or more clips for placement on dysfunctional cardiac tissue of a heart, one or more anchors for deployment and securement into the dysfunctional cardiac tissue, and a lifting mechanism for raising the one or more anchors and the dysfunctional cardiac tissue.

20 Claims, 9 Drawing Sheets

Related U.S. Application Data division of application No. 11/507,146, filed on Aug. 21, 2006, now Pat. No. 8,506,474.

(60) Provisional application No. 60/709,730, filed on Aug. 19, 2005, provisional application No. 60/709,690, filed on Aug. 19, 2005, provisional application No. 60/711,727, filed on Aug. 26, 2005.

(51) Int. Cl.
*A61B 17/00* (2006.01)
*A61B 17/04* (2006.01)
*A61B 17/128* (2006.01)
*A61B 17/064* (2006.01)
*A61B 17/068* (2006.01)
*A61B 17/06* (2006.01)
*A61B 17/30* (2006.01)

(52) U.S. Cl.
CPC ........ *A61B 17/068* (2013.01); *A61B 17/0644* (2013.01); *A61B 17/1227* (2013.01); *A61B 17/1285* (2013.01); *A61F 2/2481* (2013.01); *A61B 17/0401* (2013.01); *A61B 17/0467* (2013.01); *A61B 17/06004* (2013.01); *A61B 2017/00243* (2013.01); *A61B 2017/0404* (2013.01); *A61B 2017/0647* (2013.01); *A61B 2017/06052* (2013.01); *A61B 2017/06176* (2013.01); *A61B 2017/306* (2013.01); *A61B 2017/308* (2013.01)

(58) Field of Classification Search
CPC ........ A61B 17/12013; A61B 17/12018; A61B 17/122; A61B 17/083; A61B 2017/081; A61B 2017/086
See application file for complete search history.

(56) References Cited

U.S. PATENT DOCUMENTS

| | | | |
|---|---|---|---|
| 5,336,252 | A | 8/1994 | Cohen |
| 5,425,740 | A * | 6/1995 | Hutchinson, Jr. ..... A61B 17/122 227/902 |
| 5,482,037 | A | 1/1996 | Borghi |
| 5,755,697 | A | 5/1998 | Jones et al. |
| 5,810,884 | A | 9/1998 | Kim |
| 5,830,224 | A | 11/1998 | Cohn et al. |
| 5,865,730 | A | 2/1999 | Fox et al. |
| 5,865,791 | A * | 2/1999 | Whayne ........... A61B 17/00234 604/500 |
| 5,961,440 | A | 10/1999 | Schweich, Jr. et al. |
| 6,010,476 | A | 1/2000 | Saadat |
| 6,045,497 | A | 4/2000 | Schweich et al. |
| 6,050,936 | A | 4/2000 | Schweich, Jr. et al. |
| 6,059,715 | A | 5/2000 | Schweich, Jr. et al. |
| 6,080,182 | A | 6/2000 | Shaw et al. |
| 6,125,852 | A | 10/2000 | Stevens et al. |
| 6,155,968 | A | 12/2000 | Wilk |
| 6,162,168 | A | 12/2000 | Schweich, Jr. et al. |
| 6,165,119 | A | 12/2000 | Schweich, Jr. et al. |
| 6,165,120 | A | 12/2000 | Schweich, Jr. et al. |
| 6,166,684 | A | 12/2000 | Yoshikawa et al. |
| 6,221,104 | B1 * | 4/2001 | Buckberg .............. A61F 2/2478 600/16 |
| 6,258,021 | B1 | 7/2001 | Wilk |
| 6,260,552 | B1 | 7/2001 | Mortier et al. |
| 6,406,420 | B1 | 6/2002 | McCarthy et al. |
| 6,494,825 | B1 | 12/2002 | Talpade |
| 6,511,416 | B1 | 1/2003 | Green et al. |
| 6,572,529 | B2 | 6/2003 | Wilk |
| 6,616,684 | B1 | 9/2003 | Vidlund et al. |
| 6,623,508 | B2 | 9/2003 | Shaw et al. |
| 6,705,988 | B2 | 3/2004 | Spence et al. |
| 6,709,382 | B1 | 3/2004 | Horner |
| 6,723,038 | B1 | 4/2004 | Schroeder et al. |
| 6,746,471 | B2 | 6/2004 | Mortier et al. |
| 6,776,754 | B1 | 8/2004 | Wilk |
| 6,808,488 | B2 | 10/2004 | Mortier |
| 6,859,662 | B2 | 2/2005 | Bombardini |
| 6,890,295 | B2 | 5/2005 | Michels et al. |
| 7,146,225 | B2 | 12/2006 | Guenst et al. |
| 7,326,177 | B2 | 2/2008 | Williamson |
| 7,390,329 | B2 | 6/2008 | Westra et al. |
| 7,431,691 | B1 | 10/2008 | Wilk |
| 7,637,924 | B2 | 12/2009 | Gifford et al. |
| 7,722,523 | B2 | 5/2010 | Mortier et al. |
| 7,753,923 | B2 | 7/2010 | St Goar et al. |
| 7,766,816 | B2 | 8/2010 | Chin et al. |
| 7,785,248 | B2 | 8/2010 | Annest et al. |
| 7,942,854 | B1 | 5/2011 | Von Oepen et al. |
| 8,066,766 | B2 | 11/2011 | To et al. |
| 8,123,668 | B2 | 2/2012 | Annest et al. |
| 8,268,009 | B2 | 9/2012 | Teitelbaum et al. |
| 8,394,008 | B2 | 3/2013 | Annest et al. |
| 8,425,402 | B2 | 4/2013 | Annest et al. |
| 8,449,442 | B2 | 5/2013 | Annest et al. |
| 8,491,455 | B2 | 7/2013 | Annest et al. |
| 8,506,474 | B2 | 8/2013 | Chin et al. |
| 8,636,639 | B2 | 1/2014 | Annest et al. |
| 8,968,175 | B2 | 3/2015 | Annest et al. |
| 8,979,750 | B2 | 3/2015 | Bladel et al. |
| 8,986,189 | B2 | 3/2015 | Chin et al. |
| 9,039,594 | B2 | 5/2015 | Annest et al. |
| 9,044,231 | B2 | 6/2015 | Annest et al. |
| 9,095,363 | B2 | 8/2015 | Bladel et al. |
| 9,119,720 | B2 | 9/2015 | Chin et al. |
| 9,173,711 | B2 | 11/2015 | Butler et al. |
| 9,173,712 | B2 | 11/2015 | Annest et al. |
| 9,211,115 | B2 | 12/2015 | Annest et al. |
| 9,259,319 | B2 | 2/2016 | Chin et al. |
| 9,402,722 | B2 | 8/2016 | Annest et al. |
| 9,486,206 | B2 | 11/2016 | Annest et al. |
| 9,526,618 | B2 | 12/2016 | Chin et al. |
| 2001/0025171 | A1 | 9/2001 | Mortier et al. |
| 2001/0041821 | A1 | 11/2001 | Wilk |
| 2001/0049539 | A1 * | 12/2001 | Rehil ................... A61F 2/0063 606/151 |
| 2002/0058855 | A1 | 5/2002 | Schweich, Jr. et al. |
| 2002/0077524 | A1 | 6/2002 | Schweich, Jr. et al. |
| 2002/0077655 | A1 | 6/2002 | Frova |
| 2002/0120298 | A1 | 8/2002 | Kramer et al. |
| 2002/0123768 | A1 | 9/2002 | Gilkerson et al. |
| 2002/0169359 | A1 | 11/2002 | McCarthy et al. |
| 2002/0169360 | A1 | 11/2002 | Taylor et al. |
| 2002/0188170 | A1 | 12/2002 | Santamore et al. |
| 2002/0198563 | A1 | 12/2002 | Gainor et al. |
| 2003/0032979 | A1 | 2/2003 | Mortier et al. |
| 2003/0163165 | A1 | 8/2003 | Bornzin et al. |
| 2003/0166992 | A1 | 9/2003 | Schweich, Jr. et al. |
| 2003/0181928 | A1 | 9/2003 | Vidlund et al. |
| 2003/0181951 | A1 | 9/2003 | Cates |
| 2003/0220587 | A1 | 11/2003 | Swenson |
| 2003/0233022 | A1 | 12/2003 | Vidlund et al. |
| 2004/0064143 | A1 | 4/2004 | Hicken et al. |
| 2004/0082837 | A1 | 4/2004 | Willis |
| 2004/0088035 | A1 | 5/2004 | Guenst et al. |
| 2004/0138526 | A1 | 7/2004 | Guenst |
| 2004/0167374 | A1 | 8/2004 | Schweich |
| 2004/0167580 | A1 | 8/2004 | Mann et al. |
| 2004/0225304 | A1 | 11/2004 | Vidlund et al. |
| 2004/0267306 | A1 | 12/2004 | Blaeser et al. |
| 2005/0065506 | A1 | 3/2005 | Phan |
| 2005/0075723 | A1 | 4/2005 | Schroeder et al. |
| 2005/0096498 | A1 | 5/2005 | Houser et al. |
| 2005/0137688 | A1 | 6/2005 | Salahieh et al. |
| 2005/0143620 | A1 | 6/2005 | Mortier et al. |
| 2005/0149069 | A1 * | 7/2005 | Bertolero ................ A61B 1/12 606/151 |
| 2005/0149115 | A1 | 7/2005 | Roue et al. |
| 2005/0192599 | A1 | 9/2005 | Demarais |
| 2005/0215851 | A1 | 9/2005 | Kim et al. |
| 2005/0288613 | A1 | 12/2005 | Heil, Jr. |

(56) References Cited

U.S. PATENT DOCUMENTS

| | | |
|---|---|---|
| 2006/0004408 A1 | 1/2006 | Morris et al. |
| 2006/0079736 A1 | 4/2006 | Chin et al. |
| 2006/0131238 A1 | 6/2006 | Xu |
| 2006/0135962 A1 | 6/2006 | Kick et al. |
| 2006/0161040 A1 | 7/2006 | McCarthy et al. |
| 2006/0161238 A1 | 7/2006 | Hall |
| 2006/0167416 A1 | 7/2006 | Mathis et al. |
| 2006/0178550 A1 | 8/2006 | Jenson |
| 2006/0200002 A1 | 9/2006 | Guenst |
| 2006/0241340 A1 | 10/2006 | Schroeder et al. |
| 2006/0247672 A1 | 11/2006 | Vidlund et al. |
| 2006/0276684 A1 | 12/2006 | Speziali |
| 2007/0005018 A1 | 1/2007 | Tekbuchava |
| 2007/0010876 A1 | 1/2007 | Salahieh et al. |
| 2007/0049971 A1 | 3/2007 | Chin et al. |
| 2007/0055303 A1 | 3/2007 | Vidlund et al. |
| 2007/0073098 A1* | 3/2007 | Lenker .................. A61B 17/12 600/30 |
| 2007/0073274 A1 | 3/2007 | Chin et al. |
| 2007/0112244 A1 | 5/2007 | McCarthy et al. |
| 2007/0161846 A1 | 7/2007 | Nikotic et al. |
| 2007/0203503 A1 | 8/2007 | Salahieh et al. |
| 2007/0265658 A1 | 11/2007 | Nelson et al. |
| 2007/0287884 A1 | 12/2007 | Schena |
| 2008/0058650 A1 | 3/2008 | Saadat et al. |
| 2008/0082132 A1 | 4/2008 | Annest et al. |
| 2008/0097148 A1 | 4/2008 | Chin et al. |
| 2008/0234717 A1 | 9/2008 | Bruszewski |
| 2008/0269551 A1 | 10/2008 | Annest et al. |
| 2008/0294251 A1 | 11/2008 | Annest et al. |
| 2009/0093670 A1 | 4/2009 | Annest et al. |
| 2009/0270980 A1 | 10/2009 | Schroeder et al. |
| 2009/0287165 A1 | 11/2009 | Drapeau et al. |
| 2009/0287304 A1 | 11/2009 | Dahlgren et al. |
| 2010/0010538 A1 | 1/2010 | Juravic et al. |
| 2010/0016655 A1 | 1/2010 | Annest et al. |
| 2010/0057000 A1 | 3/2010 | Melsheimer et al. |
| 2010/0268020 A1 | 10/2010 | Chin et al. |
| 2011/0160750 A1 | 6/2011 | Annest et al. |
| 2011/0270191 A1 | 11/2011 | Paul et al. |
| 2012/0190958 A1 | 7/2012 | Annest et al. |
| 2013/0090523 A1 | 4/2013 | Van Bladel et al. |
| 2013/0090672 A1 | 4/2013 | Butler et al. |
| 2013/0090684 A1 | 4/2013 | Van Bladel et al. |
| 2013/0096579 A1 | 4/2013 | Annest et al. |
| 2013/0324787 A1 | 12/2013 | Chin et al. |
| 2013/0325041 A1 | 12/2013 | Annest et al. |
| 2014/0031613 A1 | 1/2014 | Annest et al. |
| 2014/0051916 A1 | 2/2014 | Chin et al. |
| 2014/0330296 A1 | 11/2014 | Annest et al. |
| 2014/0350417 A1 | 11/2014 | Bladel et al. |
| 2015/0066082 A1 | 3/2015 | Moshe et al. |
| 2015/0066139 A1 | 3/2015 | Bladel et al. |
| 2015/0238182 A1 | 8/2015 | Annest et al. |
| 2016/0022422 A1 | 1/2016 | Annest et al. |
| 2016/0030026 A1 | 2/2016 | Bladel et al. |
| 2016/0089132 A1 | 3/2016 | Butler et al. |
| 2016/0095600 A1 | 4/2016 | Annest et al. |
| 2016/0120648 A1 | 5/2016 | Chin et al. |
| 2016/0206427 A1 | 7/2016 | Annest et al. |
| 2016/0338835 A1 | 11/2016 | Bladel et al. |

FOREIGN PATENT DOCUMENTS

| | | |
|---|---|---|
| WO | 2002/30335 A2 | 4/2002 |
| WO | 2003/032818 A3 | 4/2003 |
| WO | 2004-043267 A2 | 5/2004 |
| WO | 2005/092203 A1 | 10/2005 |
| WO | 2006/044467 A2 | 4/2006 |
| WO | 2007/022519 A2 | 2/2007 |
| WO | 2013-049761 A1 | 4/2013 |

OTHER PUBLICATIONS

International Search Report and Written Opinion of PCT/US2012/058182, dated Mar. 1, 2013, 19 pages.
European Examination Report of EP Patent Application 05810316.9 dated Mar. 10, 2009, 6 pages.
International Search Report and Written Opinion of PCT Application No. PCT/US06/32663, dated Jul. 31, 2007, 5 pages.
International Search Report and Written Opinion of PCT Application No. PCT/US2005/036690, dated Jul. 9, 2007, 6 pages.
International Search Report and Written Opinion of PCT Application No. PCT/US09/51288, dated Sep. 15, 2009, 7 pages.
International Search Report and Written Opinion of PCT Application No. PCT/US08/64255, dated Sep. 29, 2008, 13 pages.
International Search Report and Written Opinion of PCT Application No. PCT/US06/22594, dated Oct. 1, 2008, 4 pages.
International Search Report and Written Opinion of PCT/US2012/058106, dated Nov. 26, 2012, 14 pages.
International Search Report and Written Opinion of PCT Application No. PCT/US08/78810, dated Feb. 12, 2009, 9 pages.
International Search Report and Written Opinion of PCT/US2012/58176, dated Jan. 8, 2013, 19 pages.
International Search Report and Written Opinion of PCT Application No. PCT/US12/58074, dated Mar. 13, 2013, 18 pages.
Extended European Examination Report of EP Patent Application 06802038.7 dated Nov. 12, 2013, 13 pages.
Office Action of EP Patent Application 06802038.7 dated Sep. 11, 2014, 4 pages.
International Report on Patentability of PCT/US2012/058074 dated Apr. 10, 2014, 8 pages.
International Report on Patentability of PCT/US2012/058176 dated Apr. 10, 2014, 11 npages.
USPTO—STIC Search Results—NPL (Dec. 11, 2014).
USPTO—STIC Search Results—Patents (Dec. 11, 2014).
International Search Report and Written Opinion of PCT Application No. PCT/US2014/053209 dated Mar. 2, 2015, 18 pages.
International Search Report and Written Opinion of PCT Application No. PCT/US2014/038834 dated Oct. 16, 2014, 16 pages.
International Report on Patentability of PCT Application No. PCT/US2014/038834 dated Dec. 3, 2015, 11 pages.

* cited by examiner

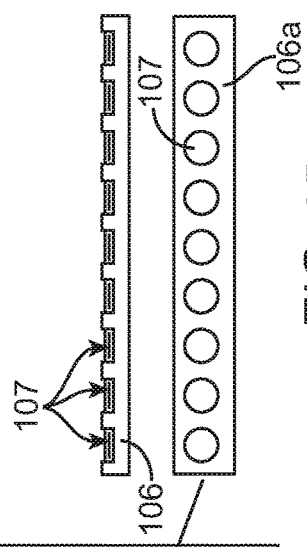
FIG. 2B
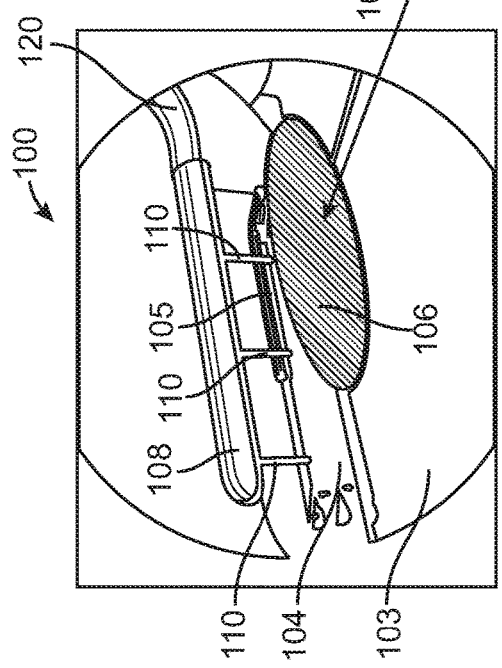
FIG. 2A
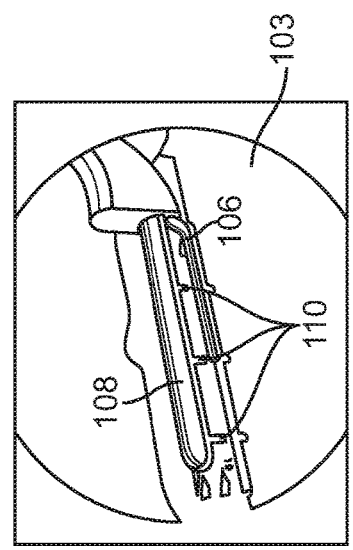
FIG. 3
FIG. 1

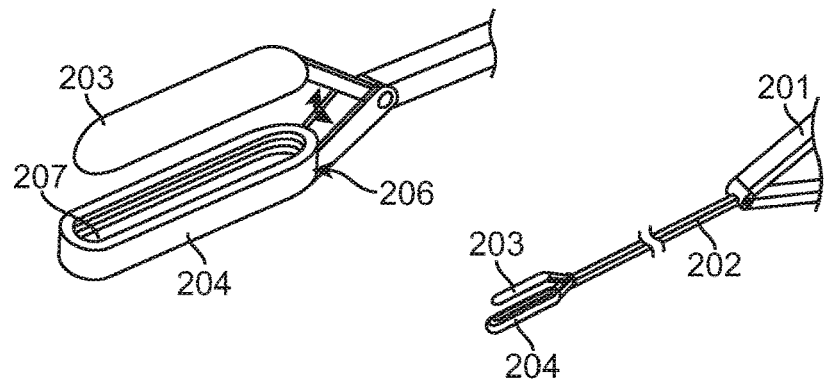
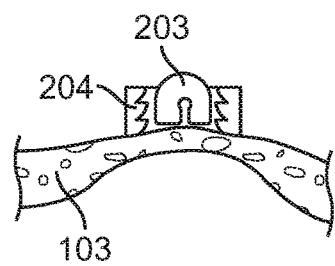 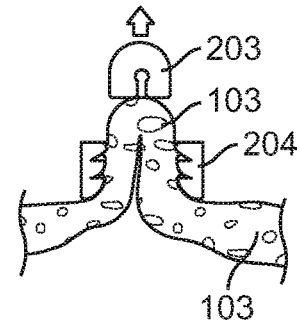
FIG. 10B    FIG. 10C
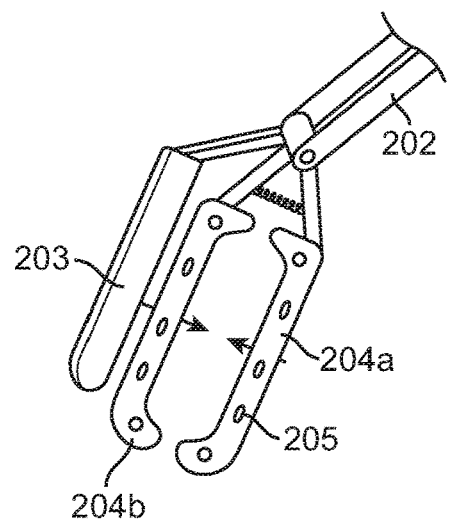
FIG. 11

PATCH W/ DEFORMABLE SLIT

METHOD AND DEVICE FOR TREATING DYSFUNCTIONAL CARDIAC TISSUE

This application is a continuation of U.S. patent application Ser. No. 13/966,049 filed on Aug. 13, 2013, which is a divisional of U.S. patent application Ser. No. 11/507,146 filed on Aug. 21, 2006, which claims the benefit of provisional patent applications Ser. No. 60/709,730 filed on Aug. 19, 2005, Ser. No. 60/709,690 filed on Aug. 19, 2005 and Ser. No. 60/711,727 filed on Aug. 26, 2005.

BACKGROUND OF THE INVENTION

Field of the Invention

This invention relates generally to devices for resizing ventricle and related methods for placing the devices. More particularly, it relates to sizing devices for reducing the ventricular volume to improve the heart's pumping action. The devices and methods of the present invention are directed toward thoracoscopy or subxiphoid techniques used to facilitate sizing of the ventricles.

Prior Art

Heart failure (HF), the heart's inability to pump an adequate volume of blood to the tissues, is the only major cardiovascular condition that continues to increase in incidence in the United States. Approximate 5 million patients are currently diagnosed with HF in the United States. The American Heart Association estimates that 550,000 new HF cases develop each year. This condition is responsible for an estimated 900,000 hospitalizations annually—more than any other medical condition among the elderly. Approximately 6.5 million hospital days each year are attributed to and related to HF and as many as one third of those patients are readmitted for treatment of symptom recurrence within 90 days. Thus, it is not surprising that the cost of providing advanced medical care for the millions of patients suffering from HF is extraordinarily high—now estimated at more than $38 billion annually.

In certain pathological conditions, the ventricles of the heart become ineffective in pumping the blood, causing a back-up of pressure in the vascular system behind the ventricle. The reduced effectiveness of the heart is usually due to an enlargement of the heart. Coronary artery disease causes approximately 60% of congestive heart failure. Acute myocardial infarction (AMI) due to obstruction of a coronary artery is a common initiating event that can lead ultimately to heart failure. A myocardial ischemia may, for example, cause a portion of a myocardium of the heart to lose its ability to contract. Prolonged ischemia can lead to infarction of a portion of the myocardium (heart muscle) wherein the heart muscle dies and become scar tissue. Once this tissue dies, it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardiwn may in fact bulge out as the heart contracts, further decreasing the hearts ability to move blood forward. When local wall motion moves in this way it is said to be dyskinetic. The dyskinetic portion of the myocardium may stretch and eventually form an aneurysmic bulge.

One problem with a large dilated left ventricle is that there is a significant increase in wall tension and/or stress both during diastolic filling and swing systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. In response, the heart tissue remodels to accommodate the chronically increased tilling pressures, further increasing the work that the now-compromised myocardium must perform. This vicious cycle of cardiac failure results in the symptoms of congestive heart failure such as shortness of breath on exertion, edema in the periphery, nocturnal dypsnia (a characteristic shortness of breath that occurs at night after going to bed), weight gain, and fatigue, to name a few. The increase in wall stress also occurs during diastolic filling. The stress increase requires a larger among of oxygen supply, which can result in exhaustion of the myocardium leading to a reduced cardiac output of the heart.

The incidence of ischemic dilated cardiomyopathy is increasing, not only as a consequence of the aging of the population, but also because effective emergency interventions for otherwise fatal acute coronary events are extending the lives of many patients with ischemic congestive heart failure (CHF). Despite the major advances in both medical and surgical therapy, the management of patients with coronary artery disease and left ventricular (LV) dysfunction continues to be challenging due to the complex and multifactorial pathophysiology of this condition.

Since heart transplantation, when indicated, continues to be limited by several factors, conventional surgical treatment for ischemic cardiomyopathy has gained increasing attention in recent years and a variety of therapeutic interventions have been developed or optimized.

It has been demonstrated that myocardial revascularization and valve repair are capable of improving left ventricular function.

Recent efforts have concentrated on improving left ventricular function by means of surgical methods aimed at ventriculoplasty with or without a reduction in ventricular volume.

Prior treatments for heart failure associated with such dilatation fall into three general categories. The first being pharmacological treatment, for example, diuretics and ACE inhibitors, The second being assist devices, for example, pumps. Finally, effective surgical treatments also have been performed with, for example, Dor or Jatene procedure, or left ventricular reconstruction (LVR), which requires the use of cardiopulmonary bypass (CPB) machine.

Many patients who would benefit from left ventricular reconstruction are the least likely to withstand the effects of CPB due to age, poor ejection fraction, or other cardiovascular disease. Therefore, there remains a need for an efficient device and method for reducing ventricular volume.

SUMMARY OF THE INVENTION

This invention relates to a device and method for completely off-pump treatment of congestive heart failure patients, and particularly, a sizing device and method for excluding infarcted tissue and reducing ventricular volume. The device and method may be performed minimally invasively which is less traumatic to the patient than an open-chest and open-heart surgical technique.

Thus, a more recent technique for treating the various forms of heart failure discussed above includes placing devices on the heart to exclude infarcted tissue and to reduce the ventricular volume. The devices are configured to reduce the ventricular volume, hence to reduce the tension in the heart wall, and thereby reverse the disease process of a failing heart.

An aspect of the present invention pertains to a clip or clamp device, and related clip methods, for thoracoscopic device placement on the heart. The clips of the present invention may be placed thoracoscopically. The inventive techniques and devices thus are minimally invasive and less risky to patients.

According to an aspect of the invention, a method for placing the clip assembly anterior a heart chamber around the infarcted tissue comprises providing a flexible and strong member having a clip or clamp and a deployable anchoring assembly connected to at least one end. The method further includes advancing an anchoring member through vasculature structure and into the heart chamber such that the first end of the anchoring member extends through infarcted tissue of a wall through the heart chamber wall and pull the infarcted tissue into or around the clip or clamp to exclude the dysfunctional tissue to reduce ventricular volume.

Yet another aspect of the invention includes a delivery tool for delivering a transventricular volume reduction device to chamber of the heart, comprising a tubular member having a distal end and proximal end, the distal end having an anchoring element and the tube defining a lumen or suture configured to carry at least a portion of the anchoring assembly. The delivery tool further includes at least one support mechanism disposed proximate the distal end of the tubular member, the support mechanism being configured to stabilize the tubular member with respect to a heart wall surrounding the chamber. The tubular member is configured to be advanced through vasculature structure and into the heart chamber.

In view of the above need for treating the dysfunctional tissue, the present invention provides a system and method incorporated into the clip or clamp device and employs small quantities of drug to be administered over an extended period of time to the heart tissues. The methods of the present invention thus avoid the pitfalls associated with systemic delivery of a drug.

A further advantage of the present invention is that it avoids problems associated with bolus injection of a drug, such as delivery of an amount of drug to the cardiac tissue, which is too high and which therefore may have deleterious effects on the cardiac tissue.

Another advantage is that it provides long-term delivery of a drug to the pericardium or myocardial tissue, with even delivery rate.

Still another important advantage is that extended delivery of a drug to the cardiac tissue can be achieved during the placement of clip or clamp for dysfunctional tissue exclusion, without the need for invasive surgery, thereby reducing trauma to the patient.

Further, in view of the above need of treating the dysfunctional tissue, the present invention provides a system and method incorporated into the clip or clamp employing transducers/sensors for determining the heart function and parameter and measuring heart performance of both left and right ventricles, particularly the left ventricle without requiring invasive surgery to access the left ventricle.

The sensors comprise at least a first sonomicrometer piezoelectric crystal mounted on a clip or clamp, so that when clip or clamp is implanted on the heart chamber, on does the sensor. One or more additional sonomicrometer piezoelectric crystals can be mounted on the clip or clamp, such that the distance between the three or more sonomicrometer crystals can be determined. In each case, the sonomicrometer crystal are distributed about a heart chamber of interest such that the distance between the separated ultrasound transmitter and receiver crystal pairs changes with contraction and relaxation of the heart chamber.

The invention thus involves the incorporation of sonomicrometer piezoelectric crystals into the clip or clamp.

A principal advantage of the system and method of the present invention include the ability to directly monitor left ventricular function without opening the left side of the heart. The system and method of the present invention is advantageously employed to measure cardiac dimensions in real time and to either record or transmit these values for monitoring purposes or to use these values as feedback to modify the delivery of electrical or pharmacological therapy, particularly in the treatment of heart failure.

The system and method of the present invention can be advantageously employed in the detection of electromechanical association during pacing or arrhythmias, differentiation of hemodynamically significant and insignificant ventricular tachycardias, monitoring of cardiac output, ventricular volume, determining the need for aggressive and less aggressive pharmacological therapies, and the like.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

FIGS. 1-9 illustrate an anchoring system used for reducing ventricular volume of a heart in accordance with an embodiment of the present invention;

FIGS. 10A-19 illustrate various other embodiments for reducing ventricular volume of a heart in accordance with the present invention.

DETAILED DESCRIPTION OF THE INVENTION

Figure 4:
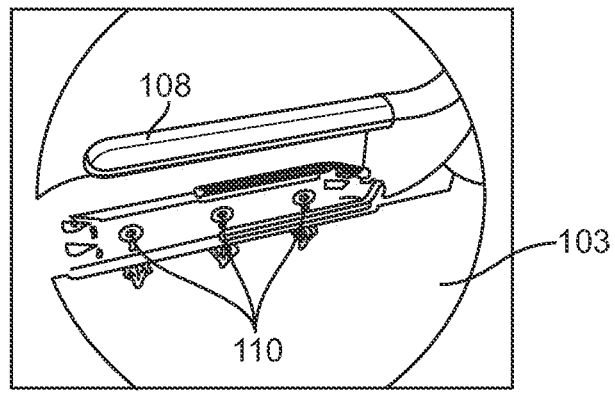

Although this invention is applicable to numerous and various types of cardiovascular methods, it has been found particularly useful in the field of reducing ventricular volume of the heart. Therefore, without limiting the applicability of the invention to the above, the invention will be described in such environment.

With reference to FIGS. 1-9, an anchoring system in accordance with one embodiment of the present invention will be described.

Initially, in FIG. 1, a subxiphoid incision is cut to create an opening 101 to access the ventricles of the heart. Additional access may be performed in the intercostal space for other instruments as well. Then, a double balloon catheter 102 is introduced into the heart through the opening 101 to unload the heart. The balloon catheter 102 provides inflow occlusion to decompress the ventricles, thereby reducing the systolic pressure for aid in reducing the ventricular volume or exclusion of dysfunctional cardiac tissue. The catheter 102 can be placed surgically in an open chest or via femoral or subclavian veins percutaneously.

As seen in FIG. 2, an anchoring mechanism 100 is then inserted through a delivery tool 120. The delivery tool 120 comprises a tubular member having a distal end and proximal end, the distal end having the anchoring mechanism 100 protruding from it. The tubular member is configured to be advanced through vasculature structure and into the heart chamber.

The anchoring mechanism 100 is brought through the delivery tool 120 and then positioned on an epicardial surface where the dysfunctional cardiac tissue 103 is located. The anchoring mechanism 100 can have a flexible bottom portion 104 with clips 105, 106, and a top portion 108 with one or more anchors 110. The clip 106 has a bottom surface 106a having pods 107, which can be seen clearly in FIG. 2b, which shows across sectional view of the clips 105, 106 with pods 107. The pods can be used to deliver hear failure drugs such as bet blocker, ACE, ARB, etc., which can be released slowly onto the dysfunctional cardiac tissue 103.

Further, several sonomicrometer crystals sensors (not shown) are located on the clips 105, 106 which are implanted in or on the patient's heart. The sensors are used for determining the heart function and parameter and measuring heart performance of both the left and right ventricles. The sensors comprise at least a first sonomicrometer piezoelectric crystal mounted on the clips 105, so that when the one or more clips 105 are implanted on the heart chamber, so does the sensor. One or more additional sonomicrometer piezoelectric crystals can be mounted on the clips 105, such that the distance between the sonomicrometer crystals can be determined. In each case, the sonomicrometer crystal are distributed about a heart chamber of interest such that the distance between the separated ultrasound transmitter and receiver crystal pairs changes with contraction and relaxation of the heart chamber.

Figure 5:
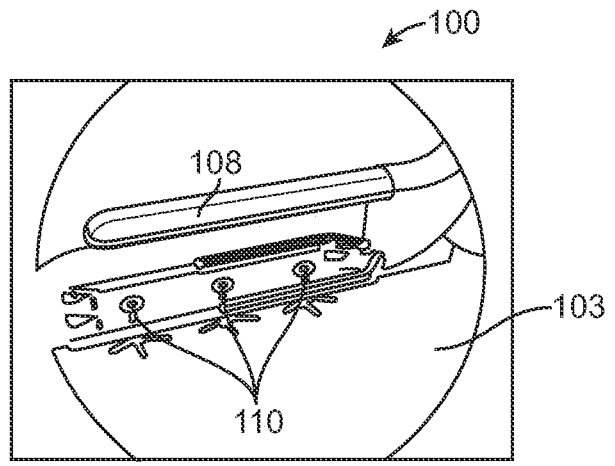

Then, as shown in FIG. 3, the anchoring mechanism 100 is inserted in the dysfunctional tissue 103. The top portion 108 is used to insert the anchors 110 through the dysfunctional tissue 103 and into the heart chamber such that a bottom end of the anchors 110 extends through the infarcted tissue into or around the clips 105. As seen in FIG. 4, the anchors 110 are slowly deployed into the dysfunctional tissue 103. In FIG. 5, anchor deployment is completed and the anchors 110 are locked into the dysfunctional tissue 103. The anchors 110 have a bottom end that deploys such that once it goes through the dysfunctional cardiac tissue 103 it opens up to secure itself to the dysfunctional cardiac tissue 103.

Figure 6:
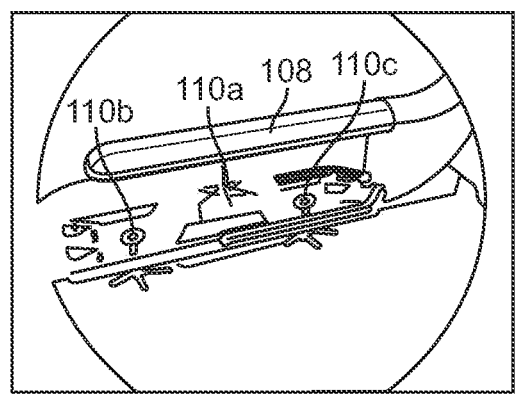
Figure 7:
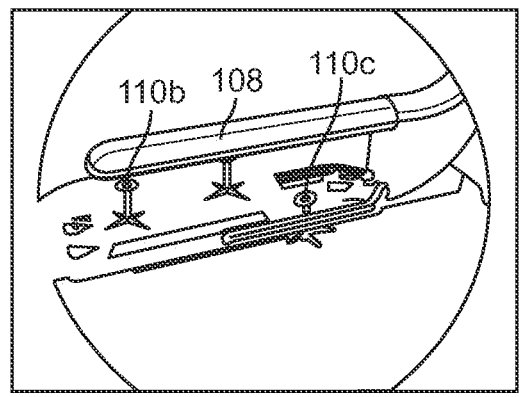
Figure 8:
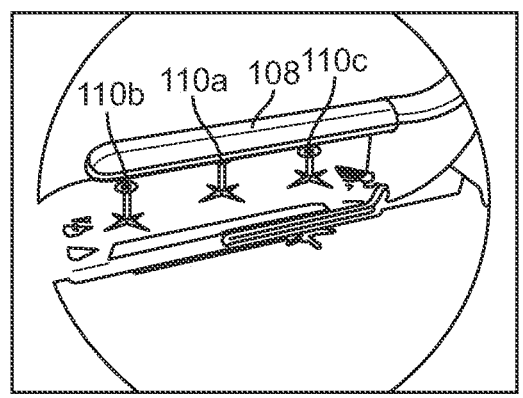

Then, as shown in FIG. 6, first the central tissue is brought up using anchor 110a. Any mechanical means can be used to raise the anchor 110a, such as a screw or clamp which can be operated by a doctor. The flexible bottom portion 104 of the anchoring mechanism 100 also rises with the anchors 110. Then, as shown in FIG. 7, the distal tissue is brought up using anchor 110b. Finally, proximal tissue 110c is brought up using anchor 110c. For purposes of the illustration, three anchors 110 are shown, although one or more can be used in the procedure. No specific order of raising the anchors 110 is required, and the anchors 110 can be raised in any order, In the preferred embodiment described above, the central anchor 110a is raised first, then the distal anchor 110b, and then the proximal anchor 110c.

Figure 9:
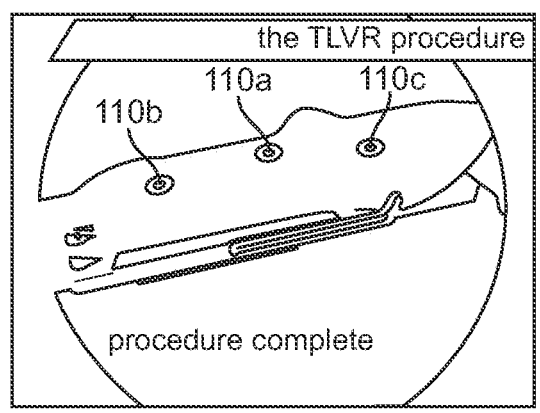

At the completion of the procedure, as shown in FIG. 9, the anchors 110 are secured. The anchors 110 can be secured using a screw thread means or any other means known in the art. The anchors 110 may be secured be a zip tag system, where the anchors are pulled together, or the anchors 110 can be clamped, or the anchors may even be glued with a bio-compatible material. The anchors 110 may, of course, be secured by any other method known in the art and are not limited to the above. The top portion 108 is retracted, and the clips 105, 106 and bottom portion 104 are left in place with the anchors 110 on the dysfunctional cardiac tissue 103 to hold the tissue in place.

The dysfunctional cardiac tissue 103 is now excluded, and the volume of the ventricle is reduced to the appropriate volume with the aid of transesophageal echocardiography (TEE) by controlling the central, proximal and/or distal anchoring mechanism 100. The clips 105 can have a controlled drug release over an extended period of time.

Various other methods and devices are also possible for reducing ventricular volume in accordance with the present invention, which will be described below with respect to FIGS. 10-19.

FIGS. 10(a)-10(c) illustrate a one way cartridge concept, where a long shaft 202 is connected to an actuator 201 at a distal end and a one-way cartridge at a proximal end. The one-way cartridge comprises a cartridge 204 and a suction head 203. The cartridge is connected to the long shaft 202 through a remotely detachable joint 206. In practice, the actuator and long shaft are inserted through a delivery tube to place the cartridge 203, 204 on dysfunctional cardiac tissue 103. The cartridge 204 is placed on the dysfunctional cardiac tissue 103, as seen in FIG. 10(b), and the suction head 204 lifts up the dysfunctional cardiac tissue 103 through the opening 207 of the cartridge 204. The cartridge 204 holds the dysfunctional cardiac tissue 103 in place and the suction cap 203 can be removed.

FIG. 11 shows a variation of the embodiment in FIG. 10, where the cartridge 204 has suction vents 205 along the top of the cartridge 204, and has interlocking parts 204a and 204b that make up the cartridge 204. Here, after the suction head 203 pulls up the dysfunctional cardiac tissue 103, the interlocking parts 204a and 204b can be pulled together to form a cartridge 204 to secure the dysfunctional cardiac tissue 103 in place.

Figure 12:
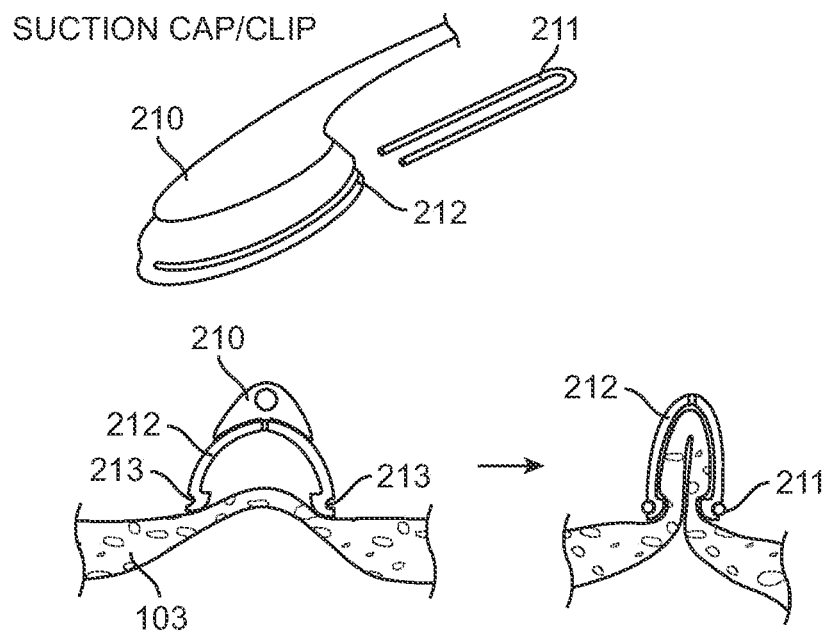

In FIG. 12, another variation of the embodiment above is described, which relies almost entirely on suction to exclude the dysfunctional cardiac tissue 103. Here, a suction cap/clip is shown having a suction cap 210, a molded silicon cap 212 and a locking clip 211. The suction cap/clip assembly is placed on the dysfunctional cardiac tissue 103 through a delivery tube, and the molded silicon cap 212 is placed on the dysfunctional cardiac tissue 103. The molded silicon cap is semi-circular in shape, and has slots 213 for the locking clip 211. The suction head 210 pulls up the dysfunctional cardiac tissue 103. The molded silicon cap 212 is then secured and squeezed in to hold the dysfunctional cardiac tissue 103 using locking clip 211 by placing the ends of the locking clip 211 through the slots 213. The suction cap 210 can then be removed, leaving the molded silicon cap 212 and locking clip 211 in place. Materials used for the cap 212 can be silicon or any other material known in the art, such as any bio-compatible material.

Figure 13:
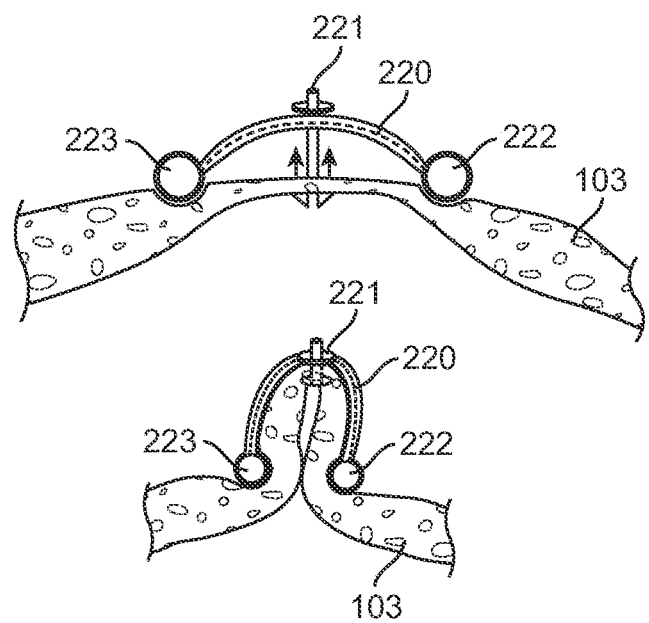

FIG. 13 shows another similar embodiment to FIG. 12, where a similar cap is placed on top of the dysfunctional cardiac tissue 103. An anchor 221 is driven through the cap 220 and through the dysfunctional cardiac tissue 103. The end of the anchor 221 has a deployment mechanism which expands once deployed through the wall of the dysfunctional cardiac tissue 103 to lock into place. The anchor 221 is then pulled up, and the cap 220 bends through forces exerted by the ends 222 and 223. The cap 220 can be such that it is under tension from ends 222 and 223, forcing it to compress and bend. Thus, once the anchor 221 is used to raise the dysfunctional cardiac tissue 103 up, the ends 222 and 223 hold the cap 220 in place, reducing the ventricular volume.

Figure 14:
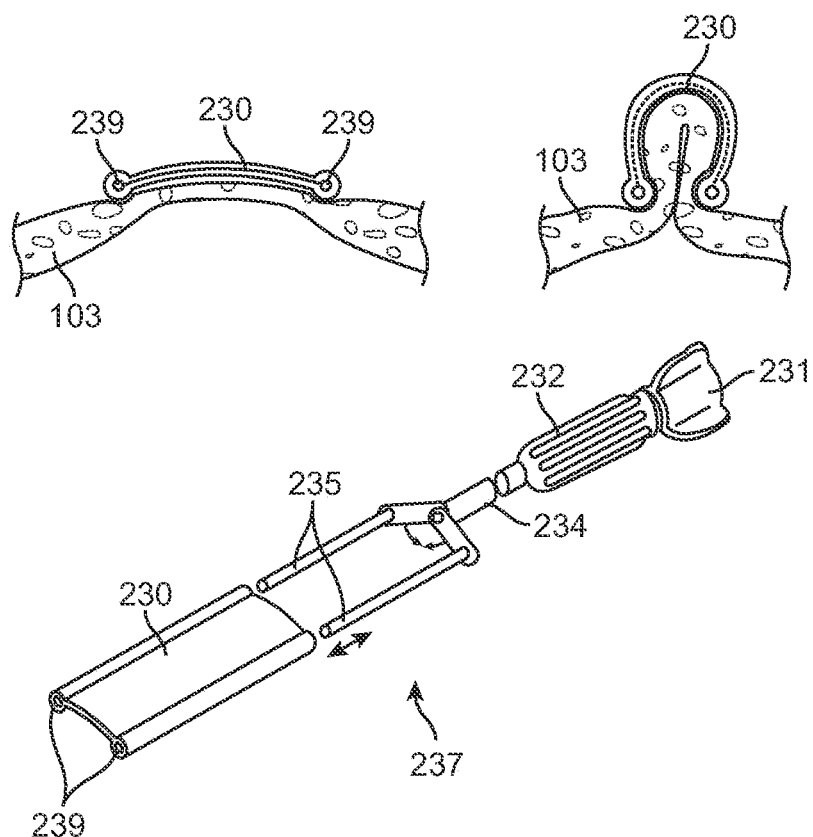

FIG. 14 shows a similar embodiment which is tightened using a tightening apparatus 237. First, a cap 230 is placed on top of dysfunctional cardiac tissue 103 using a tightening apparatus 237. The tightening apparatus comprises a knob 231, a grip 232, a long shaft 234, and force transmitting pins 235. The pins 235 connect to or go through the ends 239 of the cap 230. A spring is embedded inside the soft molded outer cover of the cap 2230. First the knob 231 is turned to rotate the pins 235, which cause the ends 239 of the cap 230 to open up and open the cap 230 and place the spring cap 230 under tension, and the cap 230 is placed on top of the dysfunctional cardiac tissue 103. Then, the knob 231 is turned in the other direction to relax spring and bring the cap 230 back to its normal position, thus squeezing in the dysfunctional cardiac tissue 103 between its ends 239. The spring in the cap 230 holds the dysfunctional cardiac tissue 103 in place and secures it into the cap 230.

Figure 15:
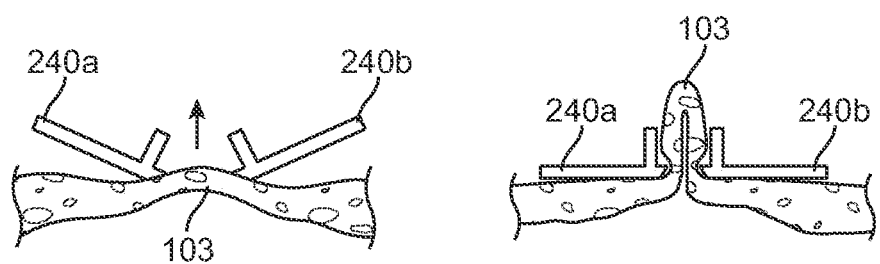

FIG. 15 shows another embodiment where two horizontal pieces 240a and 240b are placed on top of the dysfunctional cardiac tissue 103, and the dysfunctional cardiac tissue 103 is pulled up using a surgical instrument between the pieces 240a and 240b. Then, the two pieces 240a and 240b are pushed together to hold the dysfunctional cardiac tissue 103 in place, and secured by any type of locking means known in the art. The two pieces can be screwed together, nailed, tied, or any other means, FIGS. 16-18 show a transventricular anchor system where an anchor is used through a hollow tube to reduce the ventricular volume of the heart.

Figure 16:
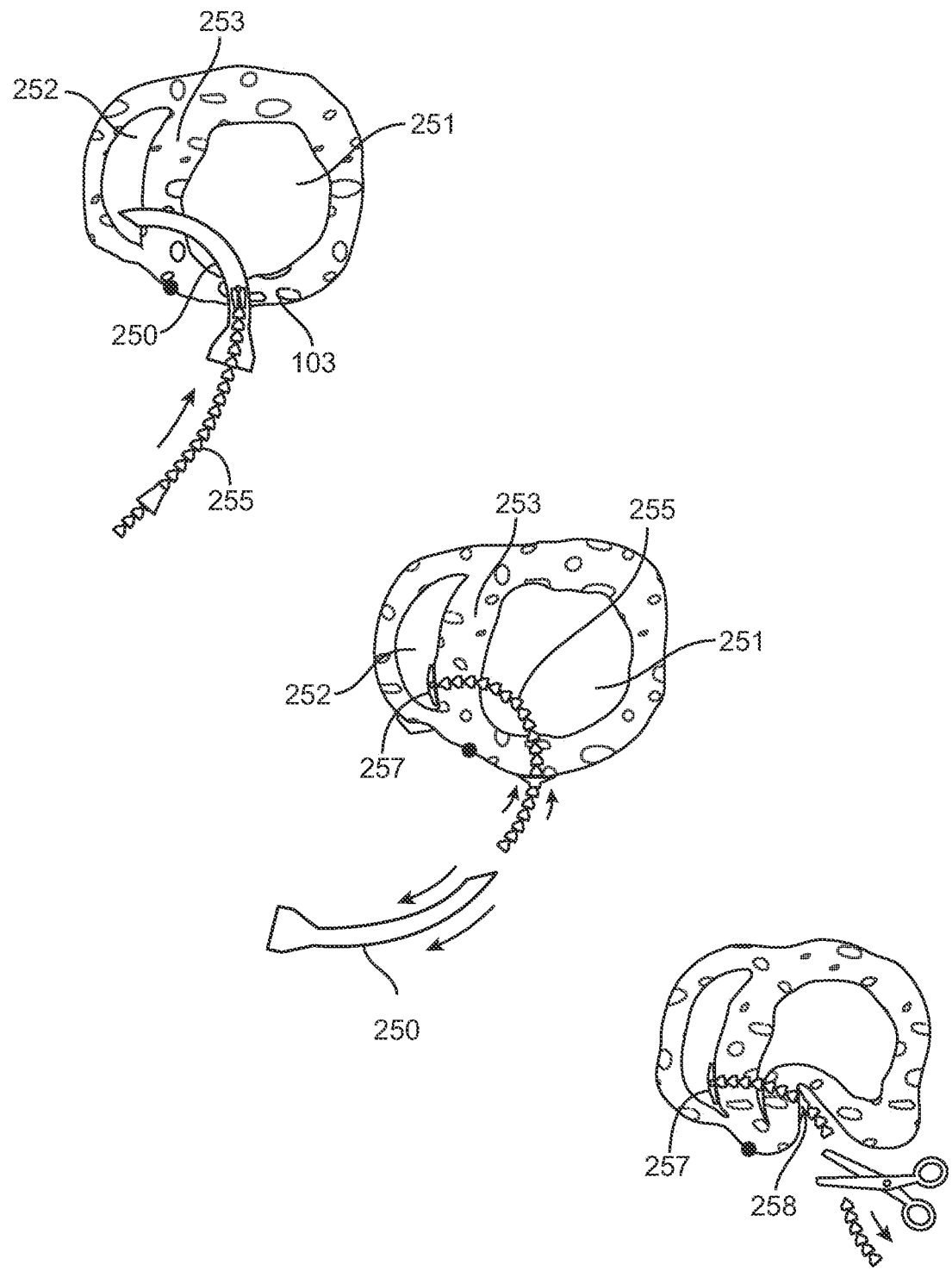

In FIG. 16, a hollow tube 250 is used to pierce through dysfunctional cardiac tissue 103, going through the left ventricle 251, through the septum 253 and into the right ventricle 252 Then, an anchor 257 is deployed having a long ratcheting member 255 attached to it. One end of the anchor 257 is secured inside the right ventricle 252 against the wall of the septum 253. The hollow tube 250 is then removed. A locking member 258 is then secured against the ratcheting member 255 and pushed along the long ratcheting member until it locks into place along the locks placed alongside the ratcheting member 255. The locking member 258 can be pushed as far as required until the ventricular walls of the left ventricle 251 are folded enough to a surgeon's preference. Any excess length of the ratcheting member 255 can then be cut off and removed.

Figure 17:
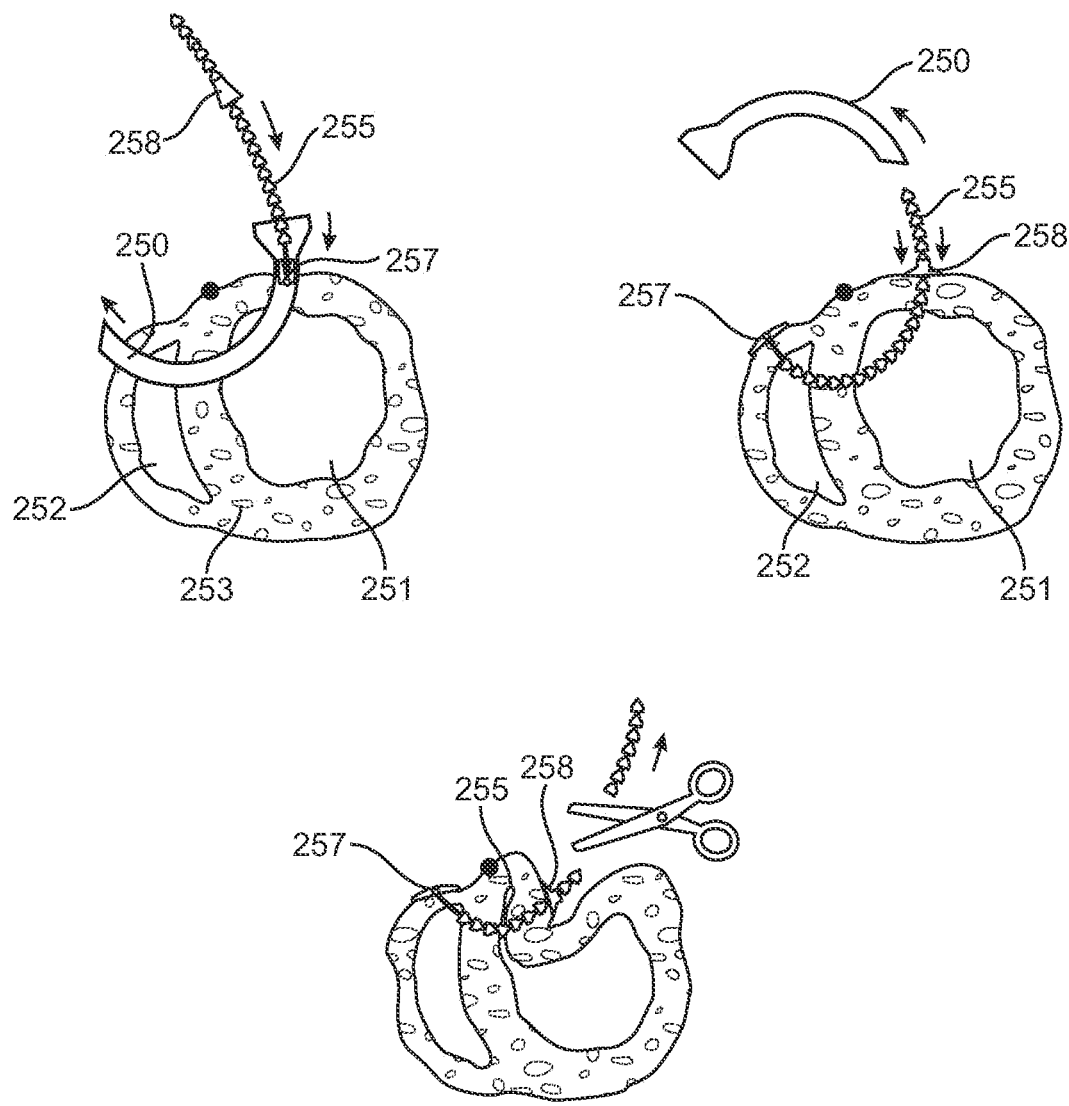

FIG. 17 shows a preferred variation of the transventricular approach from the left ventricle 251. Here, the hollow tube 250 is inserted through the left ventricle 251, through the septum 253, and through the right ventricle 252. An anchor 257 is run through the hollow tube and secured to the outside of the right ventricle 252. The anchor 257 is connected to a long ratcheting member 255. The hollow tube is then removed, and a locking member 258 running along the length of the ratcheting member 255 is secured and pushed, locking it into place against the outer wall of the left ventricle, thus reducing the volume of the left ventricle, as can be seen in FIG. 17.

Figure 18:
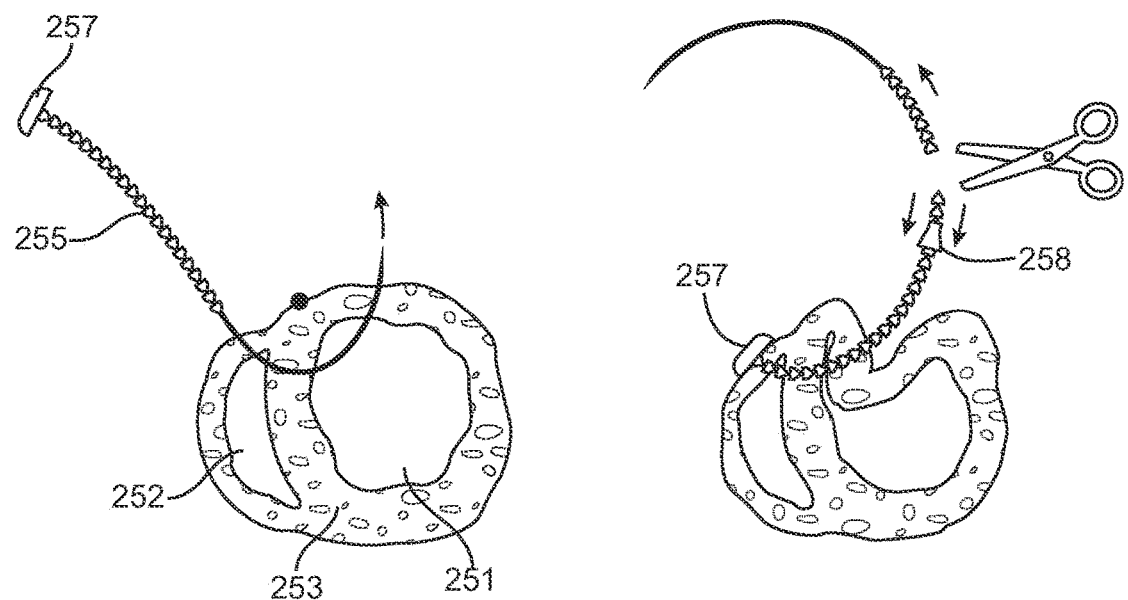

FIG. 18 shows another variation of the transventricular approach from the right ventricle 252. Again, a hollow tube 250 (not shown) is inserted through the right ventricle 252, through the septum 253 and through the left ventricle 251 all the way to the outer wall of the left ventricle 251. The hollow tube 250 is removed, leaving the ratcheting member 255 and anchor 257 behind, similar to the embodiments in FIGS. 16-17. The anchor 257 is secured against the outer wall of the right ventricle, and the locking member 258 is pushed along the length of the ratcheting member and against the wall of the left ventricle until tight, thus reducing the volume of the left ventricle, as can be seen in the figure.

Figure 19:
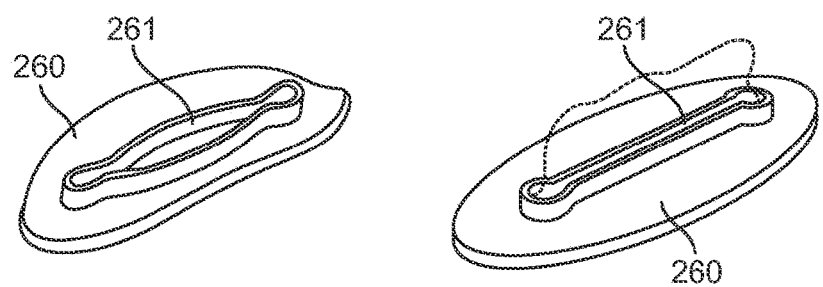

FIG. 19 shows a patch 260 with a deformable slit 261. This device is made from two components: the deformable slit 261 is formed from fully annealed stainless steel or other malleable metallic alloy and the attached patch is a woven fabric material, such as the woven fabric material sold under the trademark DACRON. The initial shape of the slit 261 has a shape similar to an elongated ellipse. The patch 260 with the deformable slit 261 is placed on the heart with the center of the slit preferably 2-3 cm from the LAD and the long axis of the slit generally parallel to the LAD. The dysfunctional tissue 103 is pulled through the slit using either one or more anchors placed through the tissue 103, or using the previously described suction device. After the desired amount of tissue 103 has been pulled through the opening, a surgical tool is used to approximate the long edges of the deformable slit 261 to hold the gathered tissue 103 in place. The effective removal of tissue from the ventricular volume and the gathering of the tissue edges together reduces the volume and short-axis diameter of the left ventricle as can be seen from the figure. The gathered tissue 103 is further secured in place by sewing the cloth material to the epicardial surface of the tissue 103 and by suturing the tissue 103 to the malleable slit 261.

The present invention provides several advantages that solve the problems with prior art methods. The device and method may be performed minimally invasively which is less traumatic to the patient than an open-chest and open-heart surgical technique, and reducing the volume of the ventricles thus reducing the tension in the heart wall and reversing the disease process of a failing heart.

Further, the clips/clamps employ small quantities of drug to be administered over an extended period of time to the heart tissue, thus avoiding the pitfalls associated with systemic delivery of a drug. The present invention avoids problems associated with bolus injection of a drug, such as delivery of an amount of drug to the cardiac tissue, which is too high and which therefore may have deleterious effects on the cardiac tissue. Another advantage is that it provides long-term delivery of a drug to the pericardium or myocardial tissue, with even delivery rate. Extended delivery of the drugs to the cardiac tissue can be achieved during the placement of the clips or clamps, without the need for invasive surgery, thereby reducing trauma to the patient.

One principal advantage of the system and method of the present invention is the ability to directly monitor left ventricular function without opening the left side of the heart. The system and method of the present invention is advantageously employed to measure cardiac dimensions in real time and to either record or transmit these values for monitoring purposes or to use these values as feedback to modify the delivery of electrical or pharmacological therapy, particularly in the treatment of heart failure. Further, the system and method of the present invention can be advantageously employed in the detection of electromechanical association during pacing or arrhythmias, differentiation of hemodynamically significant and insignificant ventricular tachycardias, monitoring of cardiac output, ventricular volume, determining the need for aggressive and less aggressive pharmacological therapies, and the like.

The above descriptions of the present invention are specific embodiments of the present invention and are not limited to the above descriptions and uses. Various sizes, numbers and types of anchors can be used. Various clips and/or clamps can be used in the anchoring mechanism. Any type of drugs can be released by the clips/clamps over various times. The anchoring system elements are not limited to what is described above, and any type of other anchoring elements can be used to deploy anchors into the dysfunctional tissue 103.

While there has been shown and described what is considered to be preferred embodiments of the invention, it will, of course, be understood that various modifications and changes in form or detail could readily be made without departing from the spirit of the invention, It is therefore intended that the invention be not limited to the exact forms described and illustrated, but should be constructed to cover all modifications that may fall within the scope of the appended claims.

What is claimed is:

1. A patch for reducing a volume of a ventricle of a heart chamber comprising:
    a main body that is positionable about dysfunctional tissue of the ventricle, the main body comprising a woven fabric material; and
    a deformable slit that extends upward from the main body, the deformable slit comprising a malleable metal material, the deformable slit having a shape of an elongated ellipse and forming a continuous, closed loop configured to allow the dysfunctional tissue to be pulled through the loop, wherein:
        the woven fabric material extends continuously around the loop;
        opposing walls of the deformable slit are configured to be displaced inwardly after the dysfunctional tissue is pulled through the loop to secure the patch about the dysfunctional tissue and reduce the volume of the ventricle; and
        the opposing walls of the deformable slit comprise a more parallel configuration after the opposing walls are displaced inwardly.

2. The patch of claim 1, wherein the malleable metal material of the deformable slit is fully annealed stainless steel.

3. The patch of claim 1, further comprising one or more anchors that are attachable to the dysfunctional tissue and that are operable to pull the dysfunctional tissue through the loop of the deformable slit.

4. The patch of claim 1, further comprising a suction device that is attachable to the dysfunctional tissue and operable to pull the dysfunctional tissue through the loop of the deformable slit.

5. The patch of claim 1, wherein the main body extends laterally and outwardly from longitudinal edges of the deformable slit.

6. The patch of claim 1, wherein the main body is attached to longitudinal edges of the deformable slit.

7. A patch for reducing a volume of a ventricle of a heart chamber comprising:
    a main body that is positionable about dysfunctional tissue of the ventricle; and
    a deformable slit that forms a continuous, closed loop, wherein the loop defines an opening that allows the dysfunctional tissue to be pulled through the opening, wherein:
        the main body is attached to the deformable slit and extends continuously around an entire periphery of the deformable slit; and
        the opening of the deformable slit is configured to be reduced after the dysfunctional tissue is pulled therethrough to secure the patch about the dysfunctional tissue and reduce the volume of the ventricle.

8. The patch of claim 7, wherein the main body comprises a woven fabric material.

9. The patch of claim 7, wherein the deformable slit comprises a malleable metal material.

10. The patch of claim 9, wherein the malleable metal material is fully annealed stainless steel.

11. The patch of claim 7, wherein the deformable slit has an initial elongated ellipse shape prior to reduction of the opening and a more parallel configuration after reduction of the opening.

12. A method for reducing a volume of a ventricle of a heart chamber, the method comprising:
    placing a patch having a deformable slit and an outward flange around the deformable slit onto dysfunctional tissue, wherein the outward flange is attached to and extends continuously around an entire periphery of the deformable slit, and wherein the patch forms a continuous, closed loop;
    pulling the dysfunctional tissue through the deformable slit on the patch; and
    securing the tissue to the deformable slit.

13. The method of claim 12, further comprising positioning the deformable slit onto the dysfunctional tissue such that a center of the deformable slit is within 2-3 cm of a left anterior descending artery (LAD).

14. The method of claim 13, wherein the deformable slit is further positioned onto the dysfunctional tissue so that a long axis of the deformable slit is generally parallel to the LAD.

15. The method of claim 12, further comprising pulling the dysfunctional tissue through the deformable slit using one or more anchors placed through the dysfunctional tissue.

16. The method of claim 12, further comprising pulling the dysfunctional tissue through the deformable slit using a suction device.

17. The method of claim 12, further comprising reducing an opening of the deformable slit after the dysfunctional tissue has been pulled through the deformable slit to hold the dysfunctional tissue in position, wherein reducing the opening of the deformable slit comprises moving opposing edges of the opening toward one another.

18. The method of claim 12, further comprising sewing the patch to an epicardial surface of the dysfunctional tissue.

19. The method of claim 18, further comprising suturing the deformable slit to the dysfunctional tissue pulled through the deformable slit.

20. The method of claim 12, wherein the outward flange is formed of at least one of a thermoplastic elastomer material or silicone.

* * * * *